(12) United States Patent
Zhao et al.

(10) Patent No.: US 12,661,555 B2
(45) Date of Patent: Jun. 23, 2026

(54) BALANCE DISORDER REHABILITATION ROBOT BASED ON VIRTUAL AND REAL SCENE FUSION

(71) Applicant: SHENYANG INSTITUTE OF AUTOMATION, CHINESE ACADEMY OF SCIENCES, Shenyang (CN)

(72) Inventors: Xingang Zhao, Shenyang (CN); Ming Zhao, Shenyang (CN); Daohui Zhang, Shenyang (CN); Bi Zhang, Shenyang (CN); Yaqi Chu, Shenyang (CN)

(73) Assignee: SHENYANG INSTITUTE OF AUTOMATION, CHINESE ACADEMY OF SCIENCES, Shenyang (CN)

( * ) Notice: Subject to any disclaimer, the term of this patent is extended or adjusted under 35 U.S.C. 154(b) by 898 days.

(21) Appl. No.: 17/906,895

(22) PCT Filed: Mar. 2, 2021

(86) PCT No.: PCT/CN2021/078568
§ 371 (c)(1),
(2) Date: Sep. 21, 2022

(87) PCT Pub. No.: WO2021/190253
PCT Pub. Date: Sep. 30, 2021

(65) Prior Publication Data
US 2023/0166159 A1     Jun. 1, 2023

(30) Foreign Application Priority Data
Mar. 23, 2020     (CN) .......................... 202010206151.8

(51) Int. Cl.
*A63B 26/00*          (2006.01)
*A61H 1/02*          (2006.01)
(Continued)

(52) U.S. Cl.
CPC ......... *A63B 26/003* (2013.01); *A61H 1/0229* (2013.01); *A63B 24/0062* (2013.01);
(Continued)

(58) Field of Classification Search
CPC .............. A63B 26/003; A63B 24/0062; A63B 24/0087; A63B 2024/009; A61H 1/0229; G16H 20/30
See application file for complete search history.

(56) References Cited

U.S. PATENT DOCUMENTS 6,162,189 A * 12/2000 Girone ................... A63B 23/08
                                                        600/595
6,558,304 B1 * 5/2003 Bardon ............ A63B 21/00178
                                                        482/148

(Continued)

FOREIGN PATENT DOCUMENTS

CN          101803988 A   *   8/2010
CN          101077451 B   *  10/2010
(Continued)

*Primary Examiner* — Xuan M Thai
*Assistant Examiner* — Andrew Bodendorf
(74) *Attorney, Agent, or Firm* — NKL Law; Allen Xue

(57) ABSTRACT

A balance disorder rehabilitation robot based on virtual and real scene fusion has a follow-up supporting device, a weight loss protection device and a virtual projection device. The follow-up supporting device is arranged in the center position of a bottom surface of the weight loss protection device and is used to follow the balance training gait of a patient in real time. The weight loss protection device is used to follow the position of center of gravity of the patient in a process of balance rehabilitation training in real time. The virtual projection device is arranged in front of the follow-up supporting device to present a virtual scene. The postures and the positions of the follow-up platforms are controlled to realize the physical sense reproduction of multiple motion
(Continued)

scenes. The physical scene is organically combined with the virtual scene to ensure a diverse balance rehabilitation training environment.

7 Claims, 5 Drawing Sheets

(51) Int. Cl.
   *A63B 24/00*            (2006.01)
   *G16H 20/30*            (2018.01)

(52) U.S. Cl.
   CPC ......... *A63B 24/0087* (2013.01); *G16H 20/30* (2018.01); *A63B 2024/009* (2013.01)

(56)                References Cited

U.S. PATENT DOCUMENTS

| | | | | |
|---|---|---|---|---|
| 8,206,267 | B2 * | 6/2012 | Holden .............. | A63B 21/4015 |
| | | | | 482/4 |
| 8,827,882 | B2 * | 9/2014 | Rogers .............. | A63B 21/4033 |
| | | | | 482/146 |
| 9,763,604 | B1 | 9/2017 | Berme et al. | |
| 9,914,003 | B2 * | 3/2018 | Kuehne .............. | A63B 71/0009 |
| 10,010,286 | B1 * | 7/2018 | Berme ................... | G01L 5/162 |
| 10,244,990 | B2 * | 4/2019 | Hu ......................... | A61B 5/112 |
| 2001/0023219 | A1 * | 9/2001 | Arnold .............. | A63B 22/0023 |
| | | | | 482/57 |
| 2006/0214911 | A1 * | 9/2006 | Miller ................... | G06F 3/038 |
| | | | | 345/157 |
| 2010/0248903 | A1 * | 9/2010 | Cardile .............. | A63B 21/0058 |
| | | | | 482/51 |
| 2010/0268129 | A1 * | 10/2010 | Park ....................... | A61H 3/008 |
| | | | | 601/35 |

| | | | | |
|---|---|---|---|---|
| 2011/0256983 | A1 * | 10/2011 | Malack .............. | A63B 21/4015 |
| | | | | 482/4 |
| 2011/0312473 | A1 * | 12/2011 | Chu ................... | A63B 69/0053 |
| | | | | 482/54 |
| 2014/0100491 | A1 * | 4/2014 | Hu ......................... | A61H 3/008 |
| | | | | 601/23 |
| 2015/0257965 | A1 * | 9/2015 | Simeone .............. | A63B 26/003 |
| | | | | 482/146 |
| 2016/0001118 | A1 * | 1/2016 | Kuehne .................. | A63B 23/04 |
| | | | | 482/54 |
| 2016/0001119 | A1 * | 1/2016 | Jue .................. | A63B 21/00069 |
| | | | | 482/54 |

FOREIGN PATENT DOCUMENTS

| | | | | | |
|---|---|---|---|---|---|
| CN | 102225033 | A | | 10/2011 | |
| CN | 102671341 | A * | 9/2012 | |
| CN | 106669117 | A | | 5/2017 | |
| CN | 106823287 | A | | 6/2017 | |
| CN | 107184374 | A | | 9/2017 | |
| CN | 107213599 | A | | 9/2017 | |
| CN | 107961496 | A * | 4/2018 | ............. A63B 71/12 |
| CN | 108324254 | A | | 7/2018 | |
| CN | 108578985 | A | | 9/2018 | |
| CN | 209451204 | U * | 10/2019 | |
| CN | 111265828 | A | | 6/2020 | |
| CN | 212141374 | U | | 12/2020 | |
| CN | 107694013 | B * | 5/2023 | .......... A63B 22/025 |
| DE | 102006035715 | A1 * | 2/2008 | .......... A61H 1/0262 |
| DE | 102013101926 | A1 | | 8/2014 | |
| KR | 100921985 | B1 * | 10/2009 | ............. A61H 3/008 |
| KR | 101778086 | B1 * | 9/2017 | ........ A63B 24/0087 |
| WO | WO-2014153016 | A1 * | 9/2014 | ........ A63B 21/4009 |
| WO | WO-2016154318 | A1 * | 9/2016 | ........ A63B 21/0059 |
| WO | WO-2021002663 | A1 * | 1/2021 | ........ A63B 71/0619 |

* cited by examiner

BALANCE DISORDER REHABILITATION ROBOT BASED ON VIRTUAL AND REAL SCENE FUSION

CROSS-REFERENCE TO RELATED APPLICATIONS

This application is a U.S. national stage entry of PCT International Application No. PCT/CN2021/078568, filed on Mar. 2, 2021, which claims the priority of Chinese Patent Application No. 202010206151.8, filed on Mar. 23, 2020, with China National Intellectual Property Administration, the content of which is incorporated herein by reference in its entirety.

TECHNICAL FIELD

The present invention relates to a medical rehabilitation training device, and particularly to a balance disorder rehabilitation robot based on virtual and real scene fusion.

BACKGROUND

Balance is a basic physiological function necessary for a human body to maintain various postures or actions, and plays a vital role in daily behavioral activities. Decreased balance function increases the falling risk of a patient, and even leads to myatrophy or loss of joint motion, thereby affecting the quality of life. The application of rehabilitation robot technology to carry out balance training to rebuild the balance ability of the patients is a research direction in recent years, and gradually advances toward practical and productized directions. However, the current balance rehabilitation device faces the problems of single training environment, insufficient personalized rehabilitation training and the like, and is urgent to further improve the adaptability and experience of the patient, and the universality of rehabilitation training modes.

SUMMARY

In view of the above problems, the purpose of the present invention is to provide a balance disorder rehabilitation robot based on virtual and real scene fusion to satisfy diversified training scenes in balance rehabilitation training and improve the effect of rehabilitation training.

To achieve the above purpose, the present invention adopts the following technical solution:

A balance disorder rehabilitation robot based on virtual and real scene fusion comprises a follow-up supporting device, a weight loss protection device and a virtual projection device, wherein the follow-up supporting device is arranged in the center position of a bottom surface of the weight loss protection device, and the follow-up supporting device is used to follow the balance training gait of a patient in real time; the weight loss protection device is used to follow the position of center of gravity of the patient in a process of balance rehabilitation training in real time; and the virtual projection device is arranged in front of the follow-up supporting device to present a virtual scene.

The follow-up supporting device comprises a follow-up platform I, a follow-up platform II and a supporting base, wherein the follow-up platform I and the follow-up platform II are left-right mirror symmetric structures, and are installed in the supporting base.

Training protection railings are arranged on both sides of the supporting base; a slope plate is installed on one end of the supporting base away from the virtual projection device; and slope railings are arranged on both sides of the slope plate.

The follow-up platform I and the follow-up platform II have the same structure, and each comprises a position adjustment platform and a posture adjustment platform arranged on the position adjustment platform; the posture adjustment platform is used for adjusting an overall posture; and the position adjustment platform is used for adjusting the height and the front and rear positions of the posture adjustment platform.

The posture adjustment platform comprises a pedal, a bottom plate and a plurality of retractable branch chains; the pedal is located above the bottom plate, and is connected with the bottom plate through the plurality of retractable branch chains; and the bottom plate is connected with the position adjustment platform.

The retractable branch chains comprise an upper connecting rod and a lower connecting rod, wherein the upper end of the upper connecting rod is hinged with the pedal, and the lower end is inserted and retractable with the upper end of the lower connecting rod; and the lower end of the lower connecting rod is hinged with the bottom plate.

The position adjustment platform comprises a translation table, a lead screw I, a belt wheel I, a belt wheel II and a transmission belt, wherein the belt wheel I and the belt wheel II are arranged on the supporting base in front and back and can rotate; the transmission belt is wound on the belt wheel I and the belt wheel II; The translation table is fixed on the transmission belt; the lead screw I is arranged along a vertical direction on the translation table, and is in threaded connection with the posture adjustment platform; and the height of the posture adjustment platform can be adjusted through the lead screw I.

The weight loss protection device comprises a supporting frame, a cross beam, a sliding table and a suspension, wherein the cross beam is arranged on the upper part of the supporting frame and can slide along front and rear directions; the sliding table is arranged on the cross beam and can slide along left and right directions; and the suspension is connected with the sliding table for connection with suspension straps.

The supporting frame is provided with a lead screw II along the front and rear directions; the lead screw II is connected with the cross beam; and the lead screw II is used for adjusting the position of the cross beam in the front and rear directions.

The virtual projection device comprises a virtual projection screen and action capturing lenses arranged on the virtual projection screen; the virtual projection screen is a curved screen; and the action capturing lenses are arranged in multiple points for capturing limb actions of a patient in the process of balance rehabilitation training.

The present invention has the advantages and positive effects that:

1. In the present invention, the angles and the motion positions of the follow-up platforms are adjusted to simulate the training scenes of level roads, steps and ramps, to realize reproduction of a variety of motion scenes in the physical sense.

2. The follow-up platforms of the present invention do not limit the ankle motion of the patient, do not hinder the subjective motion of the patient, and improve the training participation sense of the patient.

3. In the present invention, the virtual scene is projected into the screen through the virtual projection device, and the follow-up platforms are adjusted to keep the motion consistent with the virtual scene, so that the virtual scene and the physical scene are organically combined to enhance the immersion sense of balance rehabilitation training.

In the figures: 1 follow-up supporting device; 2 weight loss protection device; 3 virtual projection device; 11 follow-up platform I; 12 follow-up platform II; 13 supporting base; 14 training protection railing; 15 slope plate; 16 slope railing; 111 posture adjustment platform; 112 position adjustment platform; 1111 pedal; 1112 upper connecting rod; 1113 lower connecting rod; 1114 bottom plate; 1121 translation table; 1122 lead screw I; 1123 belt wheel I; 1124 belt wheel II; 1125 transmission belt; 21 supporting frame; 22 cross beam; 23 sliding table; 24 suspension; 211 lead screw II; 241 suspension strap; 31 virtual projection screen; and 32 action capturing lens.

DETAILED DESCRIPTION

To make the purpose, the technical solution and the advantages of the present invention more clear, the present invention will be described in detail below in detail in combination with drawings and specific embodiments.

Figure 1:
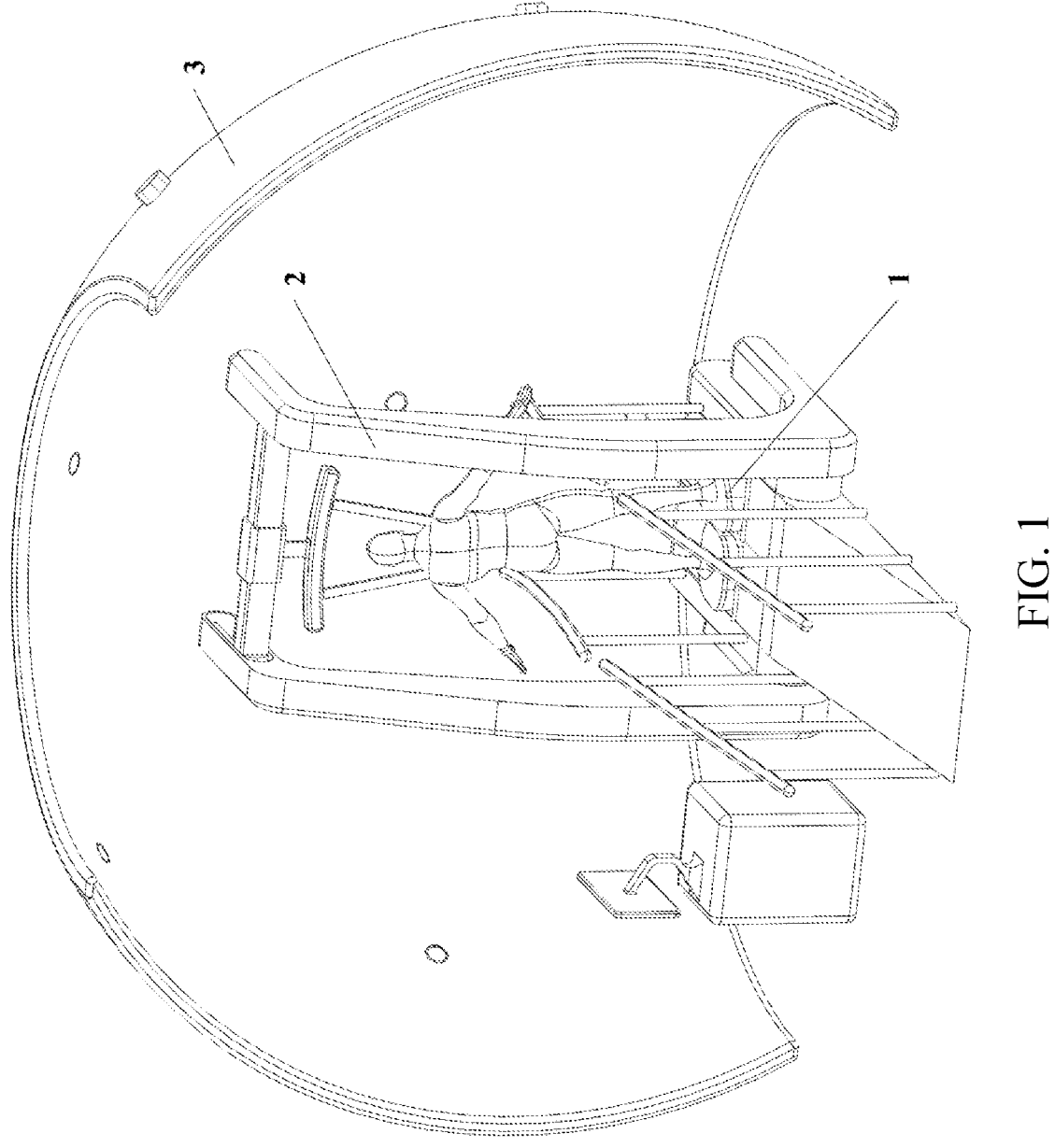
FIG. 1 is a structural schematic diagram of a balance disorder rehabilitation robot based on virtual and real scene fusion in the present invention.

As shown in FIG. 1, a balance disorder rehabilitation robot based on virtual and real scene fusion provided by the present invention comprises a follow-up supporting device 1, a weight loss protection device 2 and a virtual projection device 3, wherein the follow-up supporting device 1 is arranged in the center position of a bottom surface of the weight loss protection device 2, and the follow-up supporting device 1 is used to follow the balance training gait of a patient in real time; the weight loss protection device 2 is used to follow the position of center of gravity of the patient in a process of balance rehabilitation training in real time; and the virtual projection device 3 is arranged in front of the follow-up supporting device 1 to present a virtual scene.

Further, the virtual projection device 3 is arranged 5-8 meters in front of the follow-up supporting device 1.

Figure 2:
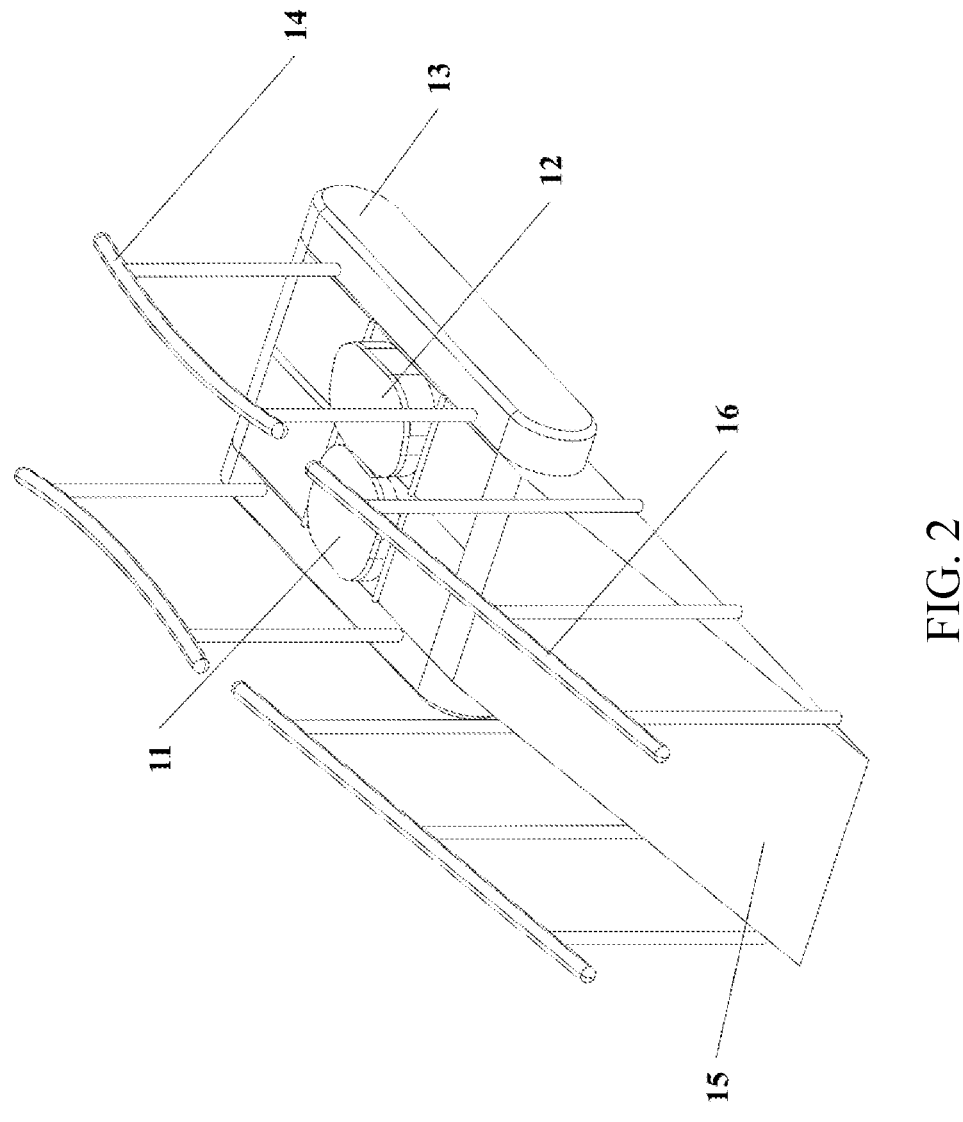
FIG. 2 is a structural schematic diagram of a follow-up supporting device in the present invention.

As shown in FIG. 2, the follow-up supporting device 1 comprises a follow-up platform I11, a follow-up platform II12 and a supporting base 13, wherein the follow-up platform I11 and the follow-up platform II12 are left-right mirror symmetric structures, and are installed in the supporting base 13. Further, training protection railings 14 are arranged on both sides of the supporting base 13 to ensure the safety of training. A slope plate 15 is installed on one end of the supporting base 13 away from the virtual projection device 3, which is convenient to guide a patient into the follow-up platform I11 and the follow-up platform II12. Slope railings 16 are arranged on both sides of the slope plate 15 to ensure the safety of the patient walking on the slope plate 15.

Figure 3:
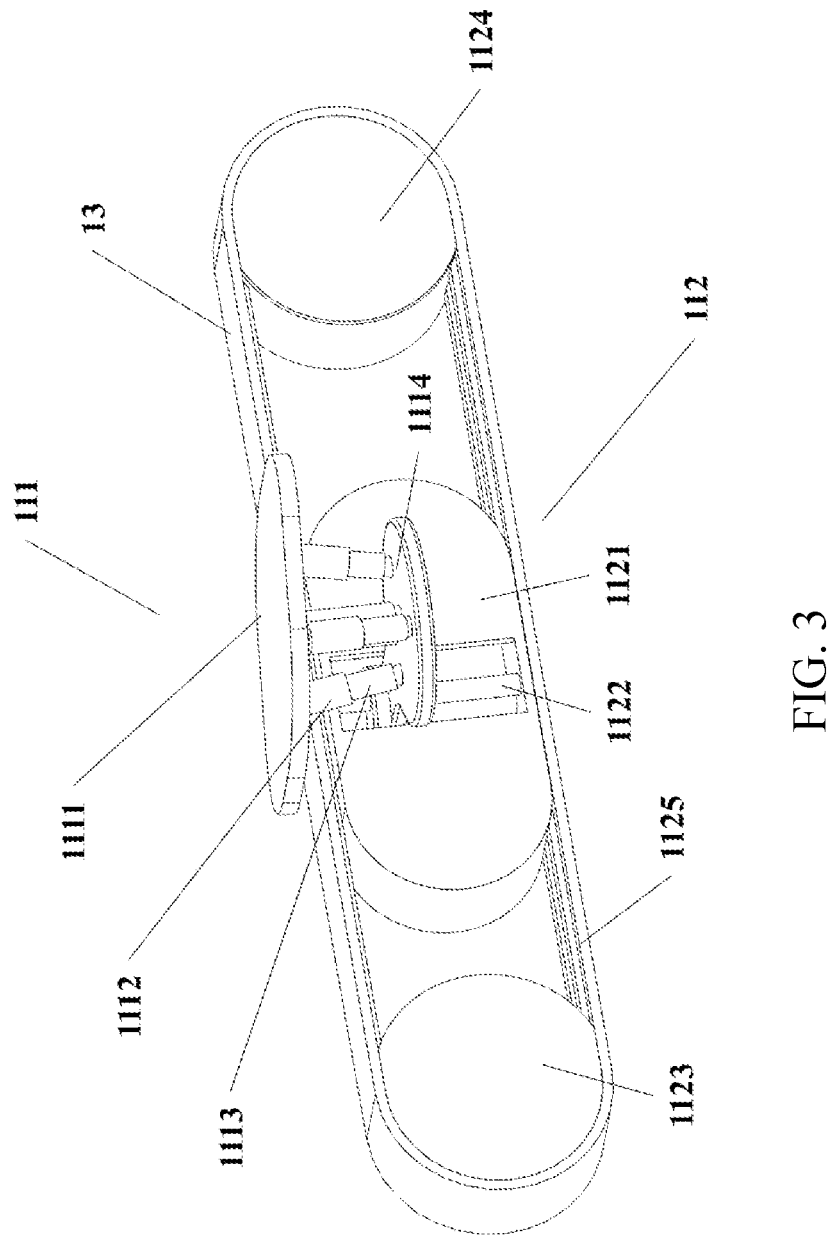
FIG. 3 is a structural schematic diagram of a follow-up platform in the present invention.

As shown in FIG. 3, the follow-up platform I11 and the follow-up platform II12 have the same structure, and each comprises a position adjustment platform 112 and a posture adjustment platform 111 arranged on the position adjustment platform 112; the posture adjustment platform 111 is used for adjusting an overall posture; and the position adjustment platform 112 is used for adjusting the height and the front and rear positions of the posture adjustment platform 111.

The posture adjustment platform 111 comprises a pedal 1111, a bottom plate 1114 and a plurality of retractable branch chains; the pedal 1111 is located above the bottom plate 1114, and is connected with the bottom plate 1114 through the plurality of retractable branch chains; and the bottom plate 1114 is connected with the position adjustment platform 112.

The retractable branch chains comprise an upper connecting rod 1112 and a lower connecting rod 1113, wherein the upper end of the upper connecting rod 1112 is hinged with the pedal 1111, and the lower end is inserted and retractable with the upper end of the lower connecting rod 1113; and the lower end of the lower connecting rod 1113 is hinged with the bottom plate 1114. The plurality of retractable branch chains are arranged to form a parallel structure; and the relative position between the upper connecting rod 1112 and the lower connecting rod 1113 in each retractable branch chain is adjusted to realize the angular change of the pedal 1111 relative to the bottom plate 1114 in all directions, so as to adjust the posture of the pedal 1111. The upper surface of the pedal 1111 is an open structure, which does not limit the ankle motion of the patient in a process of balance rehabilitation training.

The position adjustment platform 112 comprises a translation table 1121, a lead screw II122, a belt wheel I1123, a belt wheel II1124 and a transmission belt 1125, wherein the belt wheel I1123 and the belt wheel II1124 are arranged on the supporting base 13 in front and back and can rotate; the transmission belt 1125 is wound on the belt wheel II123 and the belt wheel II1124; the translation table 1121 is fixed on the transmission belt 1125; the lead screw II122 is arranged along a vertical direction on the translation table 1121, and is in threaded connection with the posture adjustment platform 111; and the height of the posture adjustment platform I11 can be adjusted through the lead screw I1122. When the belt wheel I1123 or the belt wheel II1124 rotates, the transmission belt 1125 moves and the transmission belt 1125 drives the translation table 1121 to move synchronously, to realize the front and rear displacement of the translation table 1121. The motion is transferred to the posture adjustment platform I11 through the lead screw II122 to adjust the front and rear positions of the posture adjustment platform 111 in the supporting base 13.

Figure 4:
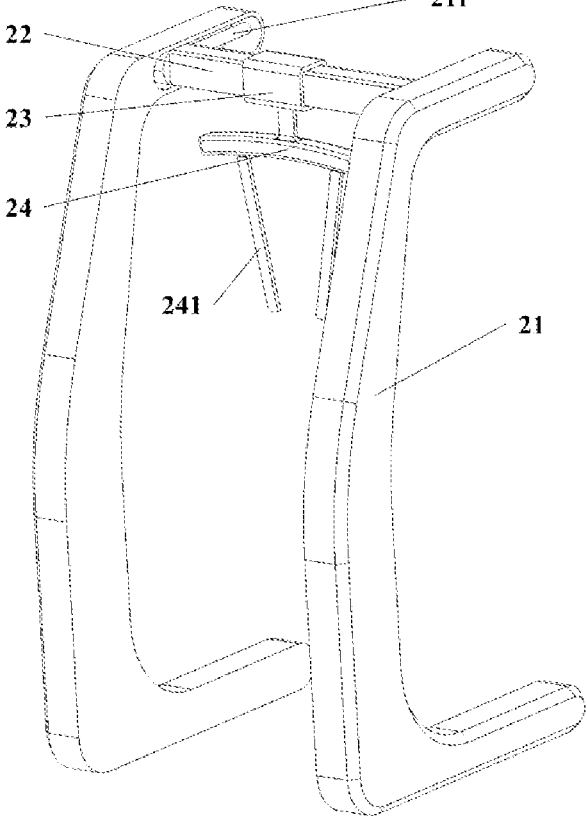
FIG. 4 is a structural schematic diagram of a weight loss protection device in the present invention.

As shown in FIG. 4, the weight loss protection device 2 comprises a supporting frame 21, a cross beam 22, a sliding table 23 and a suspension 24, wherein the cross beam 22 is arranged on the upper part of the supporting frame 21 and can slide along front and rear directions; the sliding table 23 is arranged on the cross beam 22 and can slide along left and right directions; and the suspension 24 is connected with the sliding table 23 for connection with suspension straps 241. The patient is suspended through the suspension straps 241, which can reduce the weight bearing of the patient in the process of rehabilitation training.

The supporting frame 21 is provided with a lead screw II211 along the front and rear directions; the lead screw II211 is connected with the cross beam 22; and the lead screw II211 is used for adjusting the position of the cross beam 22 in the front and rear directions.

Figure 5:
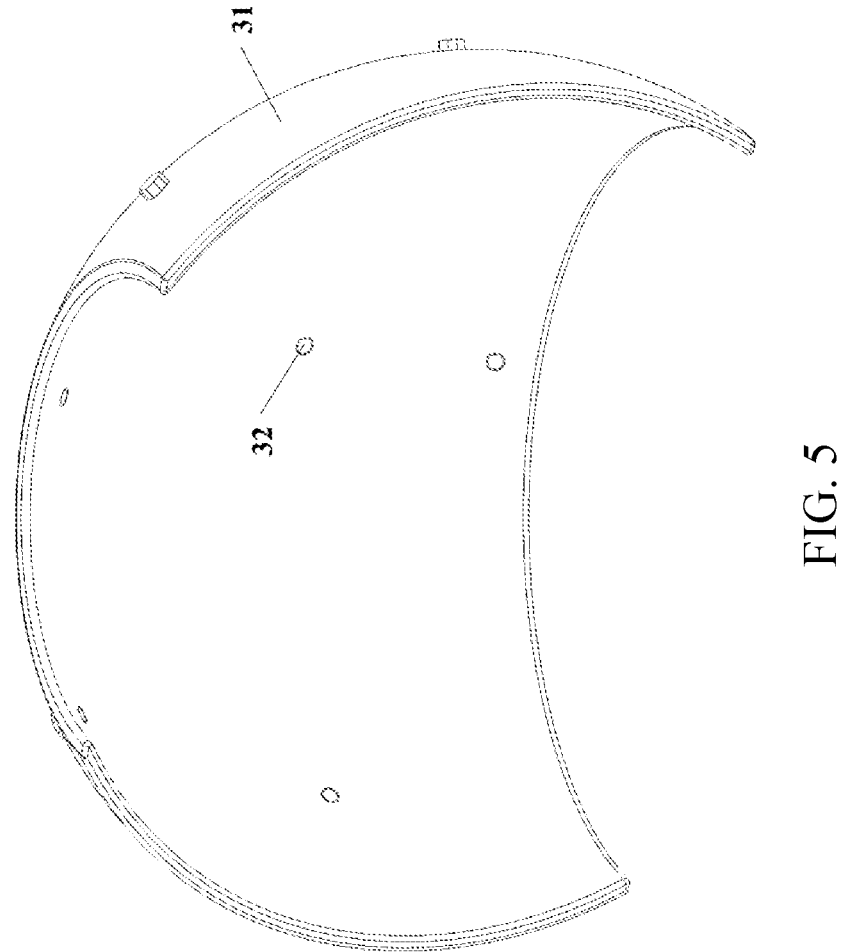
FIG. 5 is a structural schematic diagram of a virtual projection device in the present invention.

As shown in FIG. 5, the virtual projection device 3 comprises a virtual projection screen 31 and action capturing lenses 32 arranged on the virtual projection screen 31; and the virtual projection screen 31 is a curved screen for presenting a virtual scene. The action capturing lenses 32 are arranged in multiple points for capturing limb actions of the patient in the process of balance rehabilitation training.

In the present invention, the action capturing lenses 32 arranged in multiple points are used for capturing the limb actions of the patient in the process of balance rehabilitation training; the posture adjustment platform 111 and the position adjustment platform 112 are adjusted in real time; posture and position adjustment of the follow-up platform I11 and the follow-up platform II12 is realized so that the follow-up platforms can follow the balance training gait of the patient in real time; and all angles of the pedal 1111 can be adjusted through the posture adjustment platform 111 to simulate the balance rehabilitation training scenes of level roads, steps and ramps. The weight loss protection device 2 is used to follow the position of center of gravity of the patient in the process of balance rehabilitation training in real time through the mobile cross beam 22 and the sliding table 23 to keep the suspension 24 perpendicular to the ground to prevent lateral interference with the patient. The virtual projection screen 31 displays the virtual scene which is combined with the physical scene simulated by the pedal 1111 in real time.

The present invention is applicable to patients that need balance function rehabilitation, and multiple training scenes of physical simulation are combined with the projected virtual scenes in real time to enhance the immersion sense in the process of balance rehabilitation training. At the same time, the ankle motion of the patients is not limited in the training process, to provide the patients with training participation.

The above only describes the embodiments of the present invention and is not intended to limit the protection scope of the present invention. Any modification, equivalent replacement, improvement, expansion, etc. made within the spirit and the principle of the present invention shall be included within the protection scope of the present invention.

The invention claimed is:

1. A balance disorder rehabilitation robot for training a patient in need thereof, comprising:
   a follow-up supporting device (1) configured to follow gaits of the patient in real time;
   a weight loss protection device (2) disposed above the follow-up device (1); and
   a virtual projection device (3) disposed in front of the follow-up device (1),
   wherein the follow-up supporting device (1) comprises a follow-up platform I (11) and a follow-up platform II (12) installed on a supporting base (13), orientations of front, rear, left, right, above, and below are relative to a frontal axis of the patient in an upright position, having the left leg placed on the follow-up platform II (12) and the right leg placed on the follow-up platform II (12),
   wherein each of the follow-up platform I (11) and the follow-up platform II (12) comprises a position adjustment platform (112) and a posture adjustment platform (111) arranged on the position adjustment platform (112),
   wherein the posture adjustment platform (111) comprises a pedal (1111), a bottom plate (1114) and a plurality of retractable branch chains; the pedal (1111) is disposed above the bottom plate (1114) and is connected with the bottom plate (1114) through the plurality of retractable branch chains; and the bottom plate (1114) is connected with the position adjustment platform (112), and
   wherein each retractable branch chain comprises an upper connecting rod (1112) connected to the pedal (1111) and a lower connecting rod (1113) connected to the bottom plate (1114), a lower end of the upper connecting rod (1112) is inserted into and retractable from an upper end of the lower connecting rod (1113), whereby a relative position between the upper connecting rod (1112) and the lower connecting rod (1113) in each retractable branch chain is adjustable to realize angular changes of the pedal (1111) relative to the bottom plate (1114) in all directions so as to adjust a posture of the pedal (1111).

2. The balance disorder rehabilitation robot according to claim 1, wherein one training protection railing (14) is arranged on each of the left side and the right side of the supporting base (13), respectively; a slope plate (15) is installed on one end of the supporting base (13) away from the virtual projection device (3); and one slope railing (16) is arranged on each of the left side and the right side of the slope plate (15).

3. The balance disorder rehabilitation robot according to claim 1, wherein the position adjustment platform (112) comprises a translation table (1121), a lead screw I (1122), a belt wheel I (1123), a belt wheel II (1124) and a transmission belt (1125), wherein the belt wheel I (1123) and the belt wheel II (1124) are arranged on the supporting base (13) in front and back; the transmission belt (1125) is wound on the belt wheel I (1123) and the belt wheel II (1124); the translation table (1121) is affixed to the transmission belt (1125); the lead screw I (1122) is arranged in a vertical direction on the translation table (1121), and is in a threaded connection with the posture adjustment platform (111); and the height of the posture adjustment platform (111) is adjustable using the lead screw I (1122).

4. The balance disorder rehabilitation robot according to claim 1, wherein the weight loss protection device (2) comprises a supporting frame (21), a cross beam (22), a sliding table (23) and a suspension (24), wherein the cross beam (22) is arranged on the upper part of the supporting frame (21) and slidable in the front direction or the rear direction; the sliding table (23) is arranged on the cross beam (22) and is slidable along left and right directions; and the suspension (24) is connected with the sliding table (23) for connection with suspension straps (241).

5. The balance disorder rehabilitation robot according to claim 4, wherein the supporting frame (21) is provided with a lead screw II (211) connected with the cross beam (22) and configured to adjust a position of the cross beam (22) in the front direction or the rear direction.

6. The balance disorder rehabilitation robot according to claim 1, wherein the virtual projection device (3) comprises a virtual projection screen (31) and a plurality of action capturing lenses (32) arranged on the virtual projection screen (31); the virtual projection screen (31) is a curved screen; and the plurality of action capturing lenses (32) are arranged in multiple points for capturing limb actions of the patient during training.

7. The balance disorder rehabilitation robot according to claim 1, wherein the posture adjustment platform (111) comprises four retractable branch chains.

* * * * *